(12) United States Patent
Takahashi et al.

(10) Patent No.: US 9,947,520 B2
(45) Date of Patent: Apr. 17, 2018

(54) ION ANALYZER INCLUDING DETECTOR FOR DETECTING FRAGMENT IONS GENERATED BY ION-DISSOCIATION

(71) Applicant: SHIMADZU CORPORATION, Kyoto-shi, Kyoto (JP)

(72) Inventors: Hidenori Takahashi, Kyoto (JP); Kei Kodera, Kyoto (JP); Sadanori Sekiya, Kusatsu (JP); Kenichi Taniguchi, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 0 days.

(21) Appl. No.: 15/122,214

(22) PCT Filed: Feb. 17, 2015

(86) PCT No.: PCT/JP2015/054214
§ 371 (c)(1),
(2) Date: Aug. 29, 2016

(87) PCT Pub. No.: WO2015/133259
PCT Pub. Date: Sep. 11, 2015

(65) Prior Publication Data
US 2016/0372311 A1  Dec. 22, 2016

(30) Foreign Application Priority Data

Mar. 4, 2014 (JP) .................................. 2014-041206

(51) Int. Cl.
*H01J 49/16* (2006.01)
*H01J 49/06* (2006.01)
(Continued)

(52) U.S. Cl.
CPC ........ *H01J 49/0045* (2013.01); *G01N 27/622* (2013.01); *H01J 49/0072* (2013.01); *H01J 49/06* (2013.01); *H01J 49/164* (2013.01)

(58) Field of Classification Search
CPC ........... G01N 33/6848; G01N 33/6818; C07K 1/1077; C07K 1/13; H01J 49/0045;
(Continued)

(56) References Cited

U.S. PATENT DOCUMENTS 7,476,853 B2 *  1/2009  Zubarev ............. G01N 33/6848
                                                    250/281
7,582,862 B2 *  9/2009  Hartmer .............. H01J 49/145
                                                    250/281
(Continued)

OTHER PUBLICATIONS

Communication dated Dec. 2, 2016 from the European Patent Office in counterpart application No. 15758452.5.
(Continued)

*Primary Examiner* — David A Vanore
(74) *Attorney, Agent, or Firm* — Sughrue Mion, PLLC

(57) ABSTRACT

A cloud of ions captured in an ion trap (2) is irradiated with a stream of hydrogen radicals cast through a radical particle introduction hole (26) bored in a ring electrode (21) at a flow rate of $4 \times 10^{10}$ [atoms/s]. As a result, a radical induced dissociation which does not rely on the transfer or capture of electrons occurs within the ion trap (2), whereby c/z-type fragment ions are efficiently generated. After the irradiation with the hydrogen radicals, a supplemental collision-induced dissociation process may performed by introducing inert gas into the ion trap (2) and resonantly exciting the ions, in order to further promote the generation of the c/z-type fragment ions. In this manner, according to the present invention, it is possible to achieve radical induced dissociation of singly-charged ions derived from a peptide
(Continued)

and use the thereby generated c/z-type fragment ions for mass spectrometry.

20 Claims, 5 Drawing Sheets

(51) Int. Cl.
*H01J 49/00* (2006.01)
*G01N 27/62* (2006.01)

(58) Field of Classification Search
CPC ...... H01J 49/005; H01J 49/0072; H01J 49/02; H01J 49/0481; H01J 49/422; H01J 49/424
USPC ............ 250/288, 281, 282, 423 R, 424
See application file for complete search history.

(56) References Cited

U.S. PATENT DOCUMENTS

| | | | | |
|---|---|---|---|---|
| 7,723,676 B2* | 5/2010 | Vilkov | ............... | H01J 49/0045 250/281 |
| 8,034,623 B2* | 10/2011 | Oh | ............... | C07D 401/12 436/89 |
| 8,188,423 B2* | 5/2012 | Doroshenko | ....... | H01J 49/0045 250/281 |
| 8,598,514 B2* | 12/2013 | Robb | ............... | H01J 49/0054 250/281 |
| 8,604,426 B2* | 12/2013 | Hartmer | ............. | H01J 49/0072 250/281 |
| 8,932,875 B2* | 1/2015 | Cooks | ............... | H01J 49/0431 250/282 |
| 9,384,952 B2* | 7/2016 | Brown | ............... | H01J 49/0045 |
| 9,500,607 B2* | 11/2016 | Brown | ............... | H01J 49/0072 |
| 2009/0152458 A1* | 6/2009 | Vilkov | ............... | H01J 49/0045 250/282 |
| 2012/0326026 A1* | 12/2012 | Misharin | ............. | H01J 49/0013 250/283 |
| 2017/0084437 A1* | 3/2017 | Jackson | ............. | H01J 49/0072 |

OTHER PUBLICATIONS

Andrey N. Vilkov, et al., "Peptide fragmentation induced by radicals at atmospheric pressure", Journal of Mass Spectrometry, 2009, pp. 477-484, vol. 44.

Plamen A. Demirev, "Generation of Hydrogen radicals for reactivity studies in Fourier transform ion cyclotron resonance mass spectrometry", Rapid Communications in Mass Spectrometry, 2000, pp. 777-781, vol. 14.

Roman A. Zubarev, et al., "Towards an understanding of the mechanism of electron-capture dissociation: a historical perspective and modern ideas", Eur. Journal of Mass Spectrometry, 2002, pp. 337-349, vol. 8.

Alexander S. Misharin, et al., "Dissociation of peptide ions by fast atom bombardment in a quadrupole ion trap", Rapid Communications in Mass Spectrometry, 2005, pp. 2163-2171, vol. 19, issue 15.

Thomas Kocher, et al., "Fragmentation of Peptides in MALDI In-Source Decay Mediated by Hydrogen Radicals", Analytical Chemistry, 2005, pp. 172-177, vol. 77.

Danielle L. Swaney, et al., "Supplemental Activation Method for High-Efficiency Electron-Transfer Dissociation of Doubly Protonated Peptide Precursors", Analytical Chemistry, 2007, pp. 477-485, vol. 79.

International Search Report for PCT/JP2015/054214 dated Mar. 17, 2015 [PCT/ISA/210].

Written Opinion for PCT/JP2015/054214 dated Mar. 17, 2015 [PCT/ISA/237].

Written Opinion for PCT/JP2015/054214 dated Mar. 17, 2015. [PCT/ISA/237].

* cited by examiner

ION ANALYZER INCLUDING DETECTOR FOR DETECTING FRAGMENT IONS GENERATED BY ION-DISSOCIATION

CROSS REFERENCE TO RELATED APPLICATIONS

This application is a National Stage of International Application No. PCT/JP2015/054214 filed Feb. 17, 2015, claiming priority based on Japanese Patent Application No. 2014-041206 filed Mar. 4, 2014, the contents of all of which are incorporated herein by reference in their entirety.

TECHNICAL FIELD

The present invention relates to an ion analyzer for dissociating ions derived from a sample component and for analyzing the fragment ions generated by the dissociation. In particular, the ion analyzer according to the present invention is suitable for a mass spectrometer which detects fragment ions generated by dissociation after separating them according to their mass-to-charge ratios, an ion mobility spectrometer which detects fragment ions generated by dissociation after separating them according to their degrees of mobility, an ion mobility mass spectrometer composed of the two aforementioned types of devices combined together, or other similar devices.

BACKGROUND ART

In recent years, a mass spectrometric method which includes the steps of dissociating an ion derived from a target compound and detecting the thereby generated fragment ions (or product ions) after separating them according to their mass-to-charge ratios has been widely used for the identification or structural analysis of high molecular compounds. For example, an ion-trap time-of-flight mass spectrometer is commonly known as a device for such a mass spectrometry. The most popular technique for dissociating a high molecular ion captured in an ion trap in such a mass spectrometer is a low-energy collision induced dissociation (CID). For the dissociation of the ions derived from proteins or peptides, other various techniques are currently also widely used, such as electron transfer dissociation (ETD) or electron capture dissociation (ECD).

In the case of ETD, negative molecular ions are cast into the ion trap as reactant ions. Within the ion trap, the reactant ion is made to collide and interact with an ion derived from a sample component. Through this interaction, an electron is transferred from the reactant ion to a proton in the ion derived from the sample component, making the proton turn into a hydrogen radical. The radical species of the ion generated by this reaction undergoes a bond-specific dissociation. This reaction can be expressed as follows:

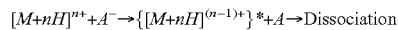

where M is the target molecule, H is the proton, A⁻ is the reactant ion, and n is a positive integer. The asterisk (*) indicates the radical state.

In the case of ECD, electrons are cast into the ion trap. Within the ion trap, the electron is added to a proton in the ion derived from the sample component. As a result, the proton turns into a hydrogen radical. The radical species of the ion generated by this reaction undergoes a bond-specific dissociation. This reaction can be expressed as follows:

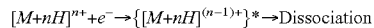

Unlike collision-type dissociation methods (such as CID), ETD and ECD are radical induced dissociation methods. In this type of dissociation, the fragmentation specifically occurs at the N-Cα bond in the peptide backbone. Therefore, c/z-type fragment ions, which cannot be easily generated by the low-energy CID, are abundantly generated. Additionally, since the fragmentation occurs with the modification sites (such as the sugar chain) retained intact, it is easy to identify the modifier or locate the modification site. This is useful for structural analyses of high molecular compounds.

However, in the ETD or ECD, as is evident from the aforementioned reaction formulae, a singly-charged ion derived from the sample component will be immediately neutralized after the radical reaction. Therefore, theoretically, only the multiply-charged ions having two or more charges can be dissociated. Furthermore, in normal situations, this technique is only effective on positive ions; it is difficult to dissociate negative ions. Additionally, since the valence of the ion decreases with each cycle of dissociation, the operation of repeating the dissociation a plurality of times to generate immonium ions including amino-acid side chains can only be applied to an ion whose valence is equal to or greater than the number of amino acid residues. Still another problem is that the technique requires a charged-particle optical system, such as an einzel lens, in order to cast charged particles (negative ions or electrons) into the ion trap.

The previously mentioned ETD and ECD are radical induced dissociation methods which use charged particles. There is also a radical induced dissociation method that uses a neutral radical particle, which is a kind of non-charged particle, in place of the charged particle. For example, Non Patent Literature 1 and Patent Literature 1 disclose a method in which a sample-component-derived ion being transported in an ambience of atmospheric pressure is irradiated with a hydroxyl radical (OH radical) to dissociate the ion.

However, the aforementioned radical induced dissociation method using the hydroxyl radical is under the constraint that the dissociation is induced in an ambience of atmospheric pressure. In commonly used mass spectrometers, the ion trap is placed in a vacuum atmosphere. Therefore, the aforementioned dissociation method cannot be used for the dissociation of an ion within such an ion trap.

Examples of the radical induced dissociation method using a neutral radical particle in a vacuum atmosphere have also been reported, e.g. in Non Patent Literatures 2 and 3. According to Non Patent Literature 2, an attempt was made to cause a radical induced dissociation in a similar manner to the ECD or ETD by casting hydrogen radicals onto singly-charged peptide ions captured in a cell of a Fourier transform ion cyclotron resonance mass spectrometer (FT-ICR MS), with the conclusion that the dissociation of the ions could not be recognized. Non Patent Literature 3 includes a report that a replication study of the experiment described in Non Patent Literature 2 was conducted, but the dissociation could also not be achieved.

Non Patent Literature 4 and Patent Literature 2 disclose a method in which an ion captured in an ion trap is dissociated by casting an accelerated beam of neutral particles or radical particles into the ion trap by using a fast atom bombardment (FAB) gun. According to the descriptions in those documents, this method works as follows: The particles accelerated to high speeds become excited and emit electrons. Those electrons adhere to the ions captured in the ion trap and induce the dissociation by a similar mechanism to the ETD or ECD.

This dissociation method does not require a charged-particle optical system to cast neutral or radical particles into the ion trap. However, despite the use of non-charged particles, this dissociation method eventually relies on the transfer or capture of electrons to induce the dissociation in a similar manner to the ETD or ECD. Therefore, in principle, the ion to be dissociated must have a charge number equal to or greater than two, which means that singly-charged ions cannot be dissociated.

CITATION LIST

Patent Literature

Patent Literature 1: U.S. Pat. No. 7,723,676 B
Patent Literature 2: U.S. Pat. No. 7,476,853 B Non Patent Literature Non Patent Literature 1: Andrey N. Vilkov and two other authors, "Peptide Fragmentation Induced by Radicals at Atmospheric Pressure", Journal of Mass Spectrometry, 2009, Vol. 44, pp. 477-484

Non Patent Literature 2: Plamen A. Demirev, "Generation of hydrogen radicals for reactivity studies in Fourier transform ion cyclotron resonance mass spectrometry", Rapid Communications in Mass Spectrometry, 2000, Vol. 14, pp. 777-781

Non Patent Literature 3: Roman A. Zubarev and four other authors, "Towards an understanding of the mechanism of electron-capture dissociation: a historical perspective and modern ideas", Journal of Mass Spectrometry, 2002, Vol. 8, pp. 337-349

Non Patent Literature 4: Alexander S. Misharin and three other authors, "Dissociation of peptide ions by fast atom bombardment in a quadrupole ion trap", Rapid Communications in Mass Spectrometry, 2005, Vol. 19, Issue 15, pp. 2163-2171

Non Patent Literature 5: T. Kocher and two other authors, "Fragmentation of peptides in MALDI in-source decay mediated by hydrogen radicals", Analytical Chemistry, 2005, Vol. 77, pp. 172-177

Non Patent Literature 6: Danielle L. Swaney and five other authors, "Supplemental Activation Method for High-Efficiency Electron-Transfer Dissociation of Doubly Protonated Peptide Precursors", Analytical Chemistry, 2007, Vol. 79, pp. 477-485

SUMMARY OF INVENTION

Technical Problem

As just described, although the radical induced dissociation method is useful for dissociating peptide molecular ions to generate c/z-type fragment ions, neither the ETD/ECD method, nor the dissociation method which uses a FAB gun to cast a beam of neutral or radical particles into the ion trap (i.e. the dissociation method disclosed in Non Patent Literature 4 or Patent Literature 2) is capable of dissociating singly-charged ions. As is commonly known, an ion generated by a matrix assisted laser desorption ionization (MALDI) or similar ionization method is normally a singly-charged ion. Therefore, an analysis technique that cannot dissociate singly-charged ions has a significantly limited range of applications. The dissociation method in which an ion derived from a sample component is irradiated with hydroxyl radicals can be applied to the dissociation of singly-charged ions. However, this method cannot be used in a vacuum atmosphere and is therefore unsuitable for the dissociation of an ion captured in an ion trap. Accordingly, this method cannot be applied in an MS$^n$ analysis with n being a value of three or greater.

The attempt of dissociating sample-component-derived ions by irradiating the ions with hydrogen radicals, which has been proposed in Non Patent Literatures 2, 3 and other documents, has not yet achieved success. Additionally, in Patent Literature 2, the method of dissociating ions by irradiating them with hydrogen radicals is also disclosed as one of a plurality of dissociation methods. However, no technical improvement is proposed to the method which has been reported in Non Patent Literatures 2 and 3 to have been unsuccessful in inducing the dissociation. Therefore, it is difficult to actually dissociate peptide molecular ions by the ion dissociation method described in Patent Literature 2.

The present invention has been developed to solve the previously described problem. Its primary objective is to provide an ion analyzer capable of dissociating singly-charged ions derived from a peptide captured in an ion trap or similar device in a vacuum atmosphere, and performing radical induced dissociation which can generate c/z-type fragment ions that cannot be easily generated by low-energy CID.

Solution to Problem

For example, similarly to the mechanism of the hydrogen adhesion reaction in the in-source decay method, when a peptide molecular ion is irradiated with hydrogen radicals (hydrogen atoms), it is expected that the hydrogen adheres to the carbonyl oxygen in the ion and forms a radical ion. Consequently, in analogy with the ETD or ECD, dissociation of the ion should occur by a reaction expressed by the following formula:

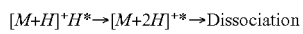

$[M+H]^+H^* \rightarrow [M+2H]^{+*} \rightarrow$ Dissociation

The dissociation method disclosed in Non Patent Literatures 2 and 3 is a method utilizing this mechanism. However, according to those documents, it was not experimentally confirmed that the dissociation actually occurs. Patent Literature 2 also does not propose any effective measure for actually inducing the dissociation.

In the conventional aforementioned attempt, hydrogen radicals are used as the radical particles for irradiating the ions. Since hydrogen radicals are highly reactive, it is possible that they easily recombine into hydrogen molecules on the inner wall of a tube, chamber wall or similar sections which guide the hydrogen radicals into the ion trap. Furthermore, when hydrogen radicals collide with the inner wall of the tube, chamber wall or similar sections, the temperature of the particles instantly decreases to approximately room temperature. In light of these points, it is expected that an attempt to cast hydrogen radicals onto ions captured in the ion trap must overcome the problem of a considerably low efficiency with which the hydrogen radicals that should contribute to the reaction can actually reach the target ions. If this is the case, it is most likely that the major cause for the unsuccessful induction of the dissociation in the conventional aforementioned attempt is the inability to secure a sufficient amount of radicals contributing the dissociating reaction.

Based on such a supposition, the present inventors repeated experiments, with the particular interest in testing various methods and conditions of introducing hydrogen radicals into the ion trap. As a result, it was confirmed that a radical induced dissociation of an ion can be achieved by efficiently introducing hydrogen radicals into the ion trap and thereby securing a sufficient amount of hydrogen radicals contributing to the reaction with the ion. The present invention has been created based on such experimental findings.

The present invention developed for solving the previously described problem is an ion analyzer for analyzing fragment ions generated by dissociating an ion derived from a sample component, including:

a) an ion-dissociating section for dissociating an ion derived from a target sample component by introducing hydrogen radicals at a flow rate of $4 \times 10^{10}$ [atoms/s] or higher into a space where the ion is present; and b) a separating and detecting section for detecting fragment ions generated by the ion-dissociating section, after separating the fragment ions according to at least either the mass-to-charge ratios or mobility of the fragment ions.

If the amount of hydrogen radicals is expressed in terms of density instead of the flow rate, the ion-dissociating section should introduce hydrogen radicals at a density of $3 \times 10^{12}$ [atoms/m$^3$] or higher into a space where the ion derived from the target sample component is present.

In other words, in the ion analyzer according to the present invention, the ion-dissociating section introduces hydrogen radicals at a flow rate of $4 \times 10^{10}$ [atoms/s] or higher, or at a density of $3 \times 10^{12}$ [atoms/m$^3$] or higher, for a predetermined period of time for an ion derived from a target sample component which is captured, for example, in an ion trap. According to an experiment conducted by the present inventors, when hydrogen radicals are introduced at a flow rate or density equal to or higher than the aforementioned level, fragment ions whose peak intensities are equal to or higher than approximately 0.1% of the peak intensity of the precursor ion can be obtained, so that fragment ion peaks can be satisfactorily detected in the mass spectrum.

The ion analyzer according to the present invention may be configured to irradiate a stream of ions derived from a sample component with hydrogen radicals to promote dissociation. However, in terms of dissociation efficiency, it is more advantageous to introduce hydrogen radicals into a comparatively small space in which a cloud of ions are confined. Accordingly, in the ion analyzer according to the present invention, the ion-dissociating section may preferably be configured to introduce the hydrogen radicals into an ion confinement section which confines ions in a specified space by the effect of a radio-frequency electric field or magnetic field, such as a three-dimensional quadrupole ion trap, a multipole linear ion trap, or a cell used in a Fourier transform ion cyclotron resonance mass spectrometer, and to make the ion derived from the target sample component react with the hydrogen radicals within the ion confinement section to dissociate the ion.

Another possible reason why the dissociation of the ion could not be confirmed in the experiment described in Non Patent Literatures 2 and 3 is that the radical particle adhered to the carbonyl oxygen in a high molecular ion forms an unwanted non-covalent bond with another atom in the three-dimensional structure of the ion and thereby prevents radical induced dissociation. This is a widely known phenomenon in the areas of ECD and ETD. With regards to this, a technique for the ETD is reported in Non Patent Literature 6, in which, after the ions captured in an ion trap are irradiated with negative ions for dissociation, a supplemental voltage is applied to the electrodes to resonantly excite the ions and make them collide with neutral particles, such as helium, to promote the radical induced dissociation.

Exciting the ions by forming a supplemental electric field in the previously described manner is also effective for improving the dissociation efficiency in the reaction of the radical particles with the confined ions in the ion analyzer according to the present invention. Accordingly, in the ion analyzer according to the present invention, when an ion trap is used as the ion confinement section, the ion-dissociating section may preferably include a supplemental dissociation promoter for promoting the dissociation of the ion captured in the ion trap by exciting the ion so as to make the ion collide with a neutral particle introduced into the ion trap, within at least either a period of time before the introduction of the hydrogen radicals or a period of time after the introduction.

For example, the excitation of the ion captured in the ion trap can be achieved by applying a predetermined resonant excitation voltage to end-cap electrodes constituting the ion trap or other electrodes corresponding to the end-cap electrodes. Laser beam irradiation may also be used as the means for exciting the ions to promote the dissociation of the ion.

In the process of introducing hydrogen radicals into the ion confinement section in the ion analyzer according to the present invention, it is advantageous to introduce those hydrogen radicals into a region where the ions are present at the highest possible density, in order to improve the dissociation efficiency. Accordingly, in the ion analyzer according to the present invention, when an ion trap is used as the ion confinement section, the ion-dissociating section may preferably perform a cooling process on the ion captured in the ion trap, using a cooling gas, before introducing the hydrogen radicals into the ion trap.

When cooled, the ions are more likely to be focused into a region around the center of the ion trap. Therefore, the dissociation efficiency can be improved by introducing hydrogen radical into the region around the center of the ion trap.

In the ion analyzer according to the present invention, if, for example, the process of irradiating the ions by introducing the hydrogen radicals into the ion confinement section is continued for an excessive length of time, an ion which has already been dissociated may undergo further dissociation, with the result that the fragment ion to be observed may be missed. Accordingly, in one mode of the ion analyzer according to the present invention, in order to prevent such multiple dissociations, the ion-dissociating section may be configured to lower the reaction rate by resonantly exciting ions included in a mass-to-charge-ratio range exclusive of a precursor ion, at least during a portion of the period of time for introducing the hydrogen radicals into the ion trap.

For example, in order to resonantly excite the ions included in the mass-to-charge-ratio range exclusive of the precursor ion, a filtered noise field (FNF) signal consisting of a superposition of component signals whose frequencies correspond to the mass-to-charge-ratio range concerned may be applied to the end-cap electrodes constituting the ion trap or other electrodes corresponding to the end-cap electrodes.

Conversely, when immonium ions originating from a single amino acid need to be observed, the dissociation may be intentionally induced a plurality of times. Accordingly, as another mode of the ion analyzer according to the present invention, the ion-dissociating section may be configured to set a long period of time for the introduction of the hydrogen radicals so as to make one ion undergo dissociation a plurality of times.

In the ion analyzer according to the present invention, in order to improve the ion dissociation efficiency, it is preferable to minimize the loss of the hydrogen radicals in the process of transporting them to the region where the ions are present (e.g. inside of the ion trap). It is generally known that the recombination of hydrogen radicals does not easily occur on a wall surface made of silicon dioxide. Accordingly, in the ion analyzer according to the present invention, the ion-dissociating section may include a hydrogen-radical introduction tube for transporting the hydrogen radicals to the region where the ion is present, the hydrogen-radical introduction tube being either a glass tube or a tube having a glass coating formed at least on the inner wall surface of the tube. This configuration reduces the loss of the hydrogen radicals due to the recombination in the process of transporting the hydrogen radicals.

In general, the temperature of the hydrogen radicals affects the reaction rate. Therefore, supplying the hydrogen radicals maintained at the highest possible temperature to the region where the ions are present is also effective for improving the ion dissociation efficiency. Accordingly, in the ion analyzer according to the present invention, the ion-dissociating section may include a hydrogen-radical introduction tube for transporting the hydrogen radicals to the region where the ion is present and a heater for maintaining the hydrogen-radical introduction tube at high temperatures or heating the same tube. By this configuration, the loss of the hydrogen radicals due to the recombination in the process of transporting the hydrogen radicals is reduced, and furthermore, the hydrogen radicals are maintained at high temperatures, so that the ion dissociation efficiency improves.

In the ion analyzer according to the present invention, a stream of inert gas may be formed along the inner wall surface of a hydrogen-radical introduction tube for transporting the hydrogen radicals to the region where the ion is present, in such a manner that the stream of inert gas prevents the hydrogen radicals from coming in contact with the inner wall surface of the introduction tube while the hydrogen radicals are transported. This configuration also reduces the loss of the hydrogen radicals due to the recombination and thereby improves the dissociation efficiency.

The ion analyzer according to the present invention may also be configured so that a stream of hydrogen radicals is directly introduced into the region where the ion is present (e.g. inside of the ion trap) without using a gas tube. To this end, the ion-dissociating section may include a flux shaper for extracting a directional stream of the hydrogen radicals. To introduce the directional stream of the hydrogen radicals extracted by the flux shaper into the inner space of a three-dimensional quadrupole ion trap, an introduction hole may be bored in the ring electrode constituting the ion trap so that a thin stream of hydrogen radicals can be introduced through this introduction hole into a region near the center of the ion trap. By this configuration, hydrogen radicals can be efficiently introduced into the ion trap while reducing the loss of the heat of the hydrogen radicals.

Advantageous Effects of the Invention

With the ion analyzer according to the present invention, even a singly-charged ion which cannot be dissociated by commonly known radical induced dissociation methods, such as the ETD or ECD, can be efficiently dissociated into fragment ions. Therefore, for example, it is possible to generate c/z-type fragment ions from a peptide molecular ion and subject them to an analysis even in a mass spectrometer or ion mobility spectrometer using an ionization method in which singly-charged ions are dominantly generated, such as the MALDI. Furthermore, since the dissociation does not rely on the transfer or capture of electrons, negative ions can also be dissociated in the same manner as positive ions.

In the ion analyzer according to the present invention, the particles used for inducing the radical induced dissociation are not charged but neutral particles. Since neutral particles are free from restriction on the introduction flow rate due to the space charge or other factors, the neutral particles for dissociation can be abundantly introduced into the region where the ions are confined by the effect of the electric field. Therefore, it is easy to improve the dissociation efficiency. An advantage also exists in terms of the device cost, since the particles for dissociation can be introduced into an ion trap (or similar device) through a commonly used gas introduction system, such as a gas tube, and it is unnecessary to use an ion optical system or similar charged-particle optical system.

Furthermore, in the ion analyzer according to the present invention, since the valence of the ion does not decrease with the dissociation of the ion, it is possible, for example, to make the target ion undergo dissociation a plurality of times by controlling the period of time for the irradiation with the hydrogen radicals. Therefore, it is easy to create immonium ions from a peptide. This is useful for the structural analyses of the peptide.

DESCRIPTION OF EMBODIMENTS

A mass spectrometer as one embodiment of the ion analyzer according to the present invention is hereinafter described with reference to the attached drawing.

Figure 1:
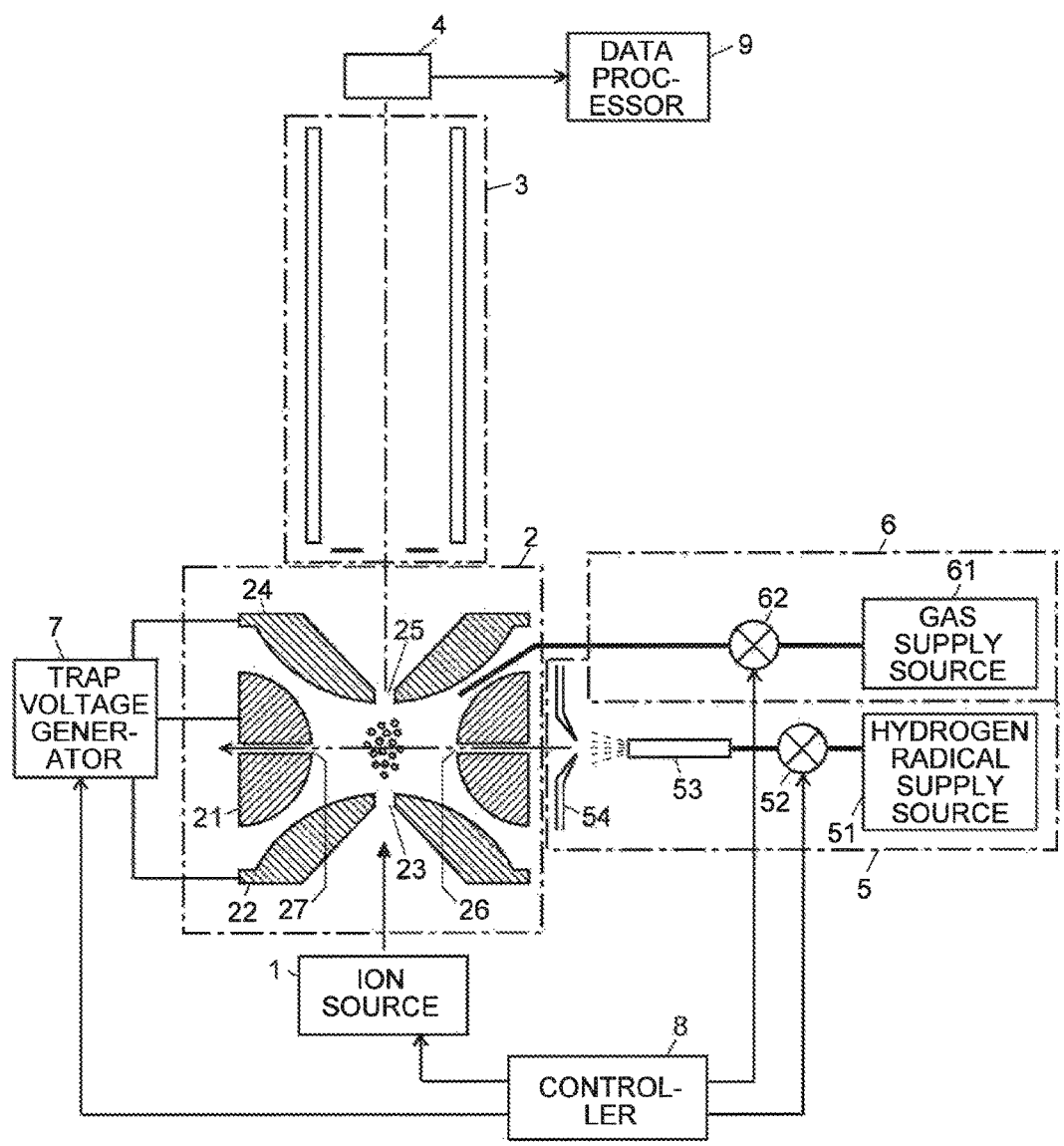
FIG. 1 is a schematic configuration diagram of a mass spectrometer as one embodiment of the ion analyzer according to the present invention.

FIG. 1 is a schematic configuration diagram of the mass spectrometer of the present embodiment.

The mass spectrometer of the present embodiment has a vacuum chamber (not shown) in which a vacuum atmosphere is maintained, with the following devices provided inside: an ion source 1 for ionizing a sample component to be analyzed; an ion trap 2 for capturing the ions generated by the ion source 1, by the effect of a radio-frequency electric field; a time-of-flight mass separator 3 for separating the ions ejected from the ion trap 2 according to their mass-to-charge ratios; and an ion detector 4 for detecting the separated ions. Additionally, the mass spectrometer of the present embodiment includes a hydrogen radical irradiator 5 for introducing hydrogen radicals into the ion trap 2 so as to dissociate ions captured in the same ion trap 2, and a gas supplier 6 for supplying a specific kind of gas into the ion trap 2.

For example, the ion source 1 is an ion source utilizing a MALDI or similar ionization method. The ion trap 2 is a three-dimensional quadrupole ion trap including an annular ring electrode 21 as well as a pair of end-cap electrodes 22 and 24 facing each other across the ring electrode 21. Under the command of a controller 8, a trap voltage generator 7 applies either a radio-frequency voltage or direct-current voltage, or a voltage composed of these two kinds of voltages, to each of the electrodes 21, 22 and 24 at a predetermined timing. The time-of-flight mass separator 3 in the present example is a linear type, although a different type of mass separator may also be used, such as a reflectron or multi-turn type. The use of the time-of-flight mass separator is not essential; for example, the ion separation function of the ion trap 2 itself may be used for the mass separation, or an orbitrap may also be used.

The hydrogen radical irradiator 5 includes: a hydrogen radical supply source 51 which holds or generates hydrogen radicals; a valve 52 with a controllable flow rate; a nozzle 53 for powerfully discharging a stream of hydrogen radicals; and a skimmer 54 having an opening located on the central axis of the stream discharged from the nozzle 53, for extracting a thin stream of hydrogen radicals from a spreading gas of hydrogen molecules and other particles.

The gas supplier 6 includes a gas supply source 61 which holds helium, argon or similar gas to be used as cooling gas, or in some cases, as the CID gas, and a valve 62 with a controllable flow rate.

An analyzing operation in the mass spectrometer of the present embodiment is hereinafter schematically described.

The various ions generated from a sample, such as a peptide mixture, in the ion source 1 are ejected from the ion source 1 in a packet-like form and introduced into the ion trap 2 through an ion introduction hole 23 formed in the entrance end-cap electrode 22. The peptide-derived ions introduced into the ion trap 2 are captured by the radio-frequency electric field formed within the ion trap 2 by the voltage applied to the ring electrode 21 from the trap voltage generator 7. After that, predetermined voltages are applied from the trap voltage generator 7 to the ring electrodes 21 and other electrodes, whereby the ions included in a mass-to-charge-ratio range exclusive of the ion having a specific mass-to-charge ratio of interest are excited, to be eventually removed from the ion trap 2. As a result, precursor ions having a specific mass-to-charge ratio are selectively captured in the ion trap 2.

Subsequently, the valve 62 in the gas supplier 6 is opened to introduce the inert gas (e.g. helium) as the cooling gas into the ion trap 2, whereby the precursor ions are cooled. As a result, the precursor ions are focused into a region around the center of the ion trap 2. In this state, the valve 52 in the hydrogen radical irradiator 5 is opened, whereupon a stream of gas containing hydrogen radicals (hydrogen atoms) is powerfully discharged from the nozzle 53. The skimmer 54 placed ahead of the discharged stream removes hydrogen gas (hydrogen molecules) and other gases, while the hydrogen radicals pass through the opening of the skimmer 54, forming a thin beam, which passes through the radical particle introduction hole 26 bored in the ring electrode 21. Eventually, the hydrogen radicals are introduced into the ion trap 2 and cast onto the precursor ions captured in the ion trap 2.

As will be described later, the opening of the valve 52 and other parameters are previously adjusted so that the flow rate of the hydrogen radicals cast onto the ions will be equal to or higher than a predetermined rate. The period of time for casting the hydrogen radicals is also previously set at an appropriate value. As a result, the precursor ions undergo radical induced dissociation, whereby c/z-type fragment ions originating from the peptide are primarily generated. The various generated fragment ions are captured in the ion trap 2, and the cooling process is performed. After that, a high direct-current voltage is applied from the trap voltage generator 7 to the end-cap electrodes 22 and 24 at a predetermined timing, whereupon the ions captured in the ion trap 2 receive acceleration energy and are simultaneously ejected through the ion ejection hole 25. In this manner, the ions having a specific amount of acceleration energy are introduced into the flight space of the time-of-flight mass separator 3. While flying through the flight space, those ions are separated according to their mass-to-charge ratios. The ion detector 4 sequentially detects the separated ions. The data processor 9 receives the detection signals and creates, for example, a time-of-flight spectrum with the point in time of the ejection of the ions from the ion trap 2 as the zero point of time. Then, using the previously determined mass calibration information, the data processor 9 converts the time-of-flight values into mass-to-charge ratios to obtain a mass spectrum formed by the fragment ions.

In the mass spectrometer of the present embodiment, the hydrogen radicals are directly cast onto the ions captured in the ion trap 2 to dissociate the ions into fragment ions. As already noted, such a dissociation method has already been attempted, as described in Non Patent Literature 2, 3 or other documents, but has not yet achieved success. This type of dissociation method is also disclosed in Patent Literature 2, but no measure for actually achieving a successful dissociation is proposed in it. In light of such backgrounds, the present inventors have experimentally searched for a condition for dissociating the ions by directly casting hydrogen radicals onto the ions, and have eventually confirmed that a satisfactory dissociation can occur under an appropriate condition.

Hereinafter, the detailed configuration of the mass spectrometer of the present embodiment as well as more preferable configurations will be described, along with the explanation of the result of the experiment.

[Actual Measurement 1]

Figure 2:
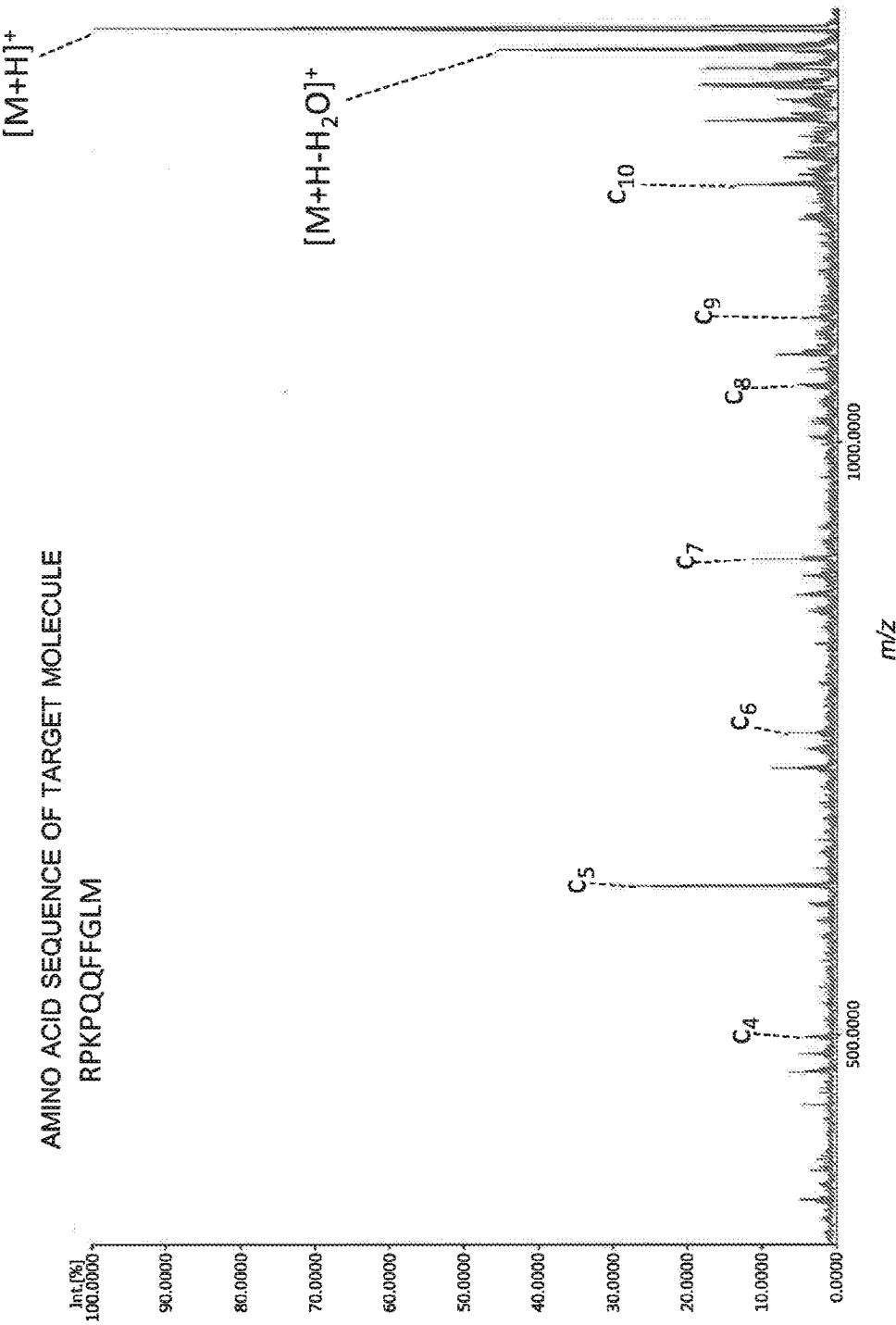
FIG. 2 is a measured example of the mass spectrum of the fragment ions obtained by dissociating singly-charged ions captured in an ion trap by a reaction with hydrogen radicals.

FIG. 2 shows a measured example of the mass spectrum of the fragment ions generated by casting hydrogen radicals onto singly-charged ions of substance-P (molecular formula: $C_{63}H_{98}N_{18}O_{13}S$, amino acid sequence: RPKPQQFFGLM) captured in the ion trap 2 in the mass spectrometer of the present embodiment. In this actual measurement, hydrogen radicals were cast onto the ions captured in the ion trap 2 at a flow rate of approximately $1.3 \times 10^{13}$ [atoms/sec] for 8 seconds. As shown in FIG. 2, c-type fragment peaks were clearly observed. Normally, c-type ions will not be generated by CID in which the dissociation into fragment ions is induced by collision with neutral particles. For comparison, another experiment was conducted in which only hydrogen molecules with no hydrogen radicals contained were cast onto the ions in the ion trap 2. No c-type fragment peaks as shown in FIG. 2 were observed. From these measurement results, it is possible to conclude that the radical induced dissociation utilizing the interaction between hydrogen radicals and ions has been achieved, at least in the configuration shown in FIG. 1 and under the aforementioned conditions.

Normally, in CID, it is often the case that the dissociation specifically occurs at a site near a basic amino acid. Therefore, the sequence of the fragment ion peaks in which the number of amino acid residues changes in steps may not be obtained in the mass spectrum. By contrast, in the mass spectrum obtained in the previously described measurement, all fragment ion peaks from $c_4$ to $c_{10}$ are obtained within the mass-to-charge-ratio range higher than the low-mass cutoff of the ion trap 2. This means that the amino acid sequence is non-specifically cut, as with the ETD or ECD. The sequence of the fragment ion peaks obtained in this manner is extremely useful for the structural analysis of peptides, because it facilitates the estimation of the amino acid sequence based on the mass-to-charge-ratio difference between the neighboring peaks (or other kinds of information).

In this measurement, the contaminant ions which were remaining in the ion trap 2 even after the process of selecting the precursor ions in the ion trap 2 (i.e. the ions which could not be completely removed by the precursor-ion selection process) were removed by applying an FNF signal to the end-cap electrodes 22 and 24 before the casting of the hydrogen radicals onto the ions captured in the ion trap 2 was initiated. Therefore, no fragment ion peaks which originate from contaminant ions should be present in the mass spectrum shown in FIG. 2. Accordingly, it is possible to conclude that all fragment ion peaks observed in FIG. 2 have originated from the target precursor ions.

An experiment aimed at improving the dissociation efficiency of the c/z type was also conducted. In this experiment, after the hydrogen radicals were cast onto the ions to promote their dissociation, helium (or argon) gas was introduced from the gas supplier 6 into the ion trap 2, and a predetermined resonant excitation voltage was applied from the trap voltage generator 7 to the end-cap electrodes 22 and 24 to excite the precursor ions remaining in the non-dissociated form in the ion trap 2 and thereby make them collide with the gas. The result demonstrated that the intensities of the c/z-type fragment ion peaks increased to several times the previous values. This means that the generation of the c/z-type fragment ions can be promoted by performing a supplemental CID operation on the precursor ions which remain in the non-dissociated form in the ion trap 2 even after the irradiation with the hydrogen radicals. The mechanism of this phenomenon remains to be clarified. One possible cause is that hydrogen atoms which have adhered to the ions in a different state from the bonded state necessary for radical induced dissociation receive additional energy from the outside and promote the radical induced dissociation.

Accordingly, in the mass spectrometer of the present embodiment, after the radical induced dissociation process is performed by casting hydrogen radicals onto the ions captured in the ion trap 2 for a predetermined period of time, the previously described supplemental CID operation may be performed, and the fragment ions obtained by such a two-stage dissociation may be captured in the ion trap 2 as the target of the mass spectrometry.

Although the skimmer 54 is provided in the hydrogen radical irradiator 5, hydrogen molecules ($H_2$) will inevitably be supplied to the ion trap 2 along with the hydrogen radicals at almost the same flow rate as the hydrogen radicals. Hydrogen molecules do not contribute to the reaction for dissociation; actually, they deteriorate the degree of vacuum in the ion trap 2 and may possibly lower the ion-capturing efficiency in the ion trap 2 as well as deteriorate the mass-resolving power. However, as long as the flow rate is at such low levels as in the previously described experiment, the introduction of the hydrogen molecules into the ion trap 2 does not significantly affect the degree of vacuum in the vacuum chamber. Indeed, in the previously described experiment, the degree of vacuum around the ion trap 2 was maintained at approximately $1 \times 10$ Pa, and no adverse effect on the ion-capturing efficiency and mass-resolving power was recognized.

[Actual Measurement 2]

Figure 3:
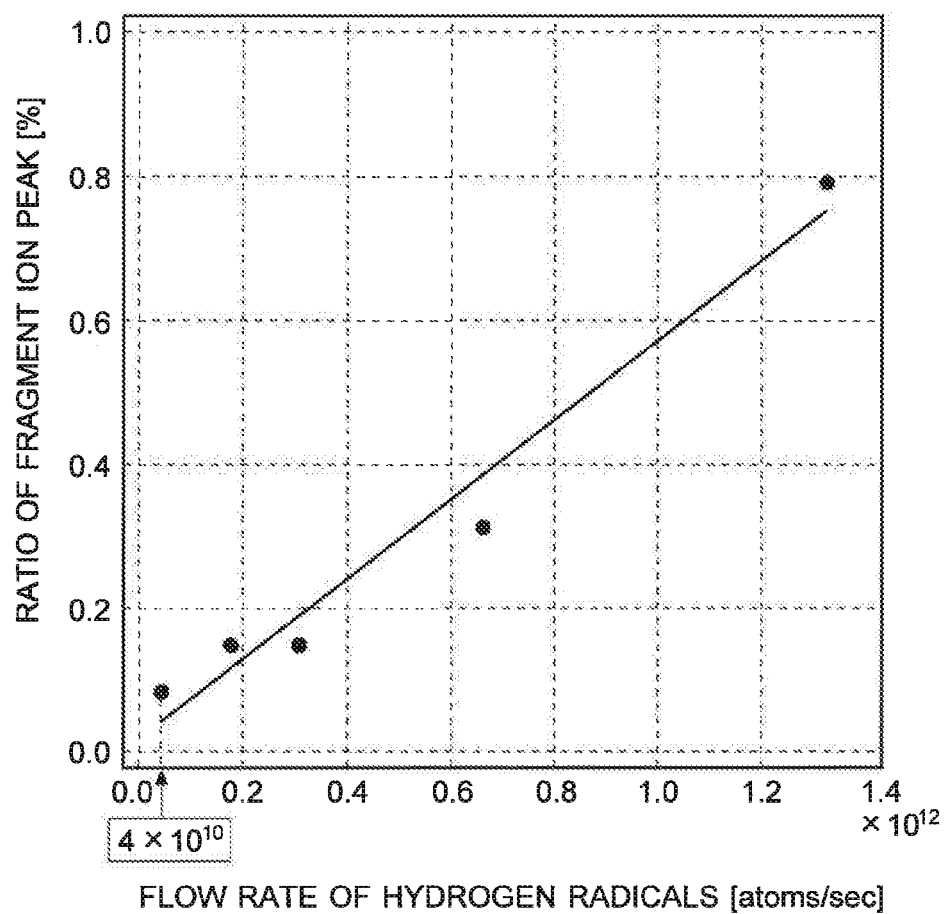
FIG. 3 is a graph showing a measured result of the relationship between the flow rate of the hydrogen radicals introduced into an ion trap and the peak intensity of the fragment ions.

FIG. 3 is a measured result of the relationship between the flow rate of the hydrogen radicals cast onto the ions in the ion trap 2 and the fragment-peak intensity characteristics. The ions to be dissociated were the same as in the previous experiment, substance-P. The vertical axis represents the ratio of the peak intensity of the $c_5$ fragment ion, which had the highest SN ratio among those obtained from the singly-charged ions of substance-P, to the peak intensity of the precursor ion. The peak intensity of the precursor ion used in the calculation was 68 mV, which is the value obtained by a preliminary experiment conducted with no casting of the hydrogen radicals. The horizontal axis in FIG. 3 represents the absolute value of the flow rate of the hydrogen radicals. A quadrupole mass spectrometer was used to measure this absolute value of the flow rate of the hydrogen radicals. The noise component in this actual measurement was approximately 0.02 mV. The SN ratio of the precursor ion was approximately 3500.

Figure 4:
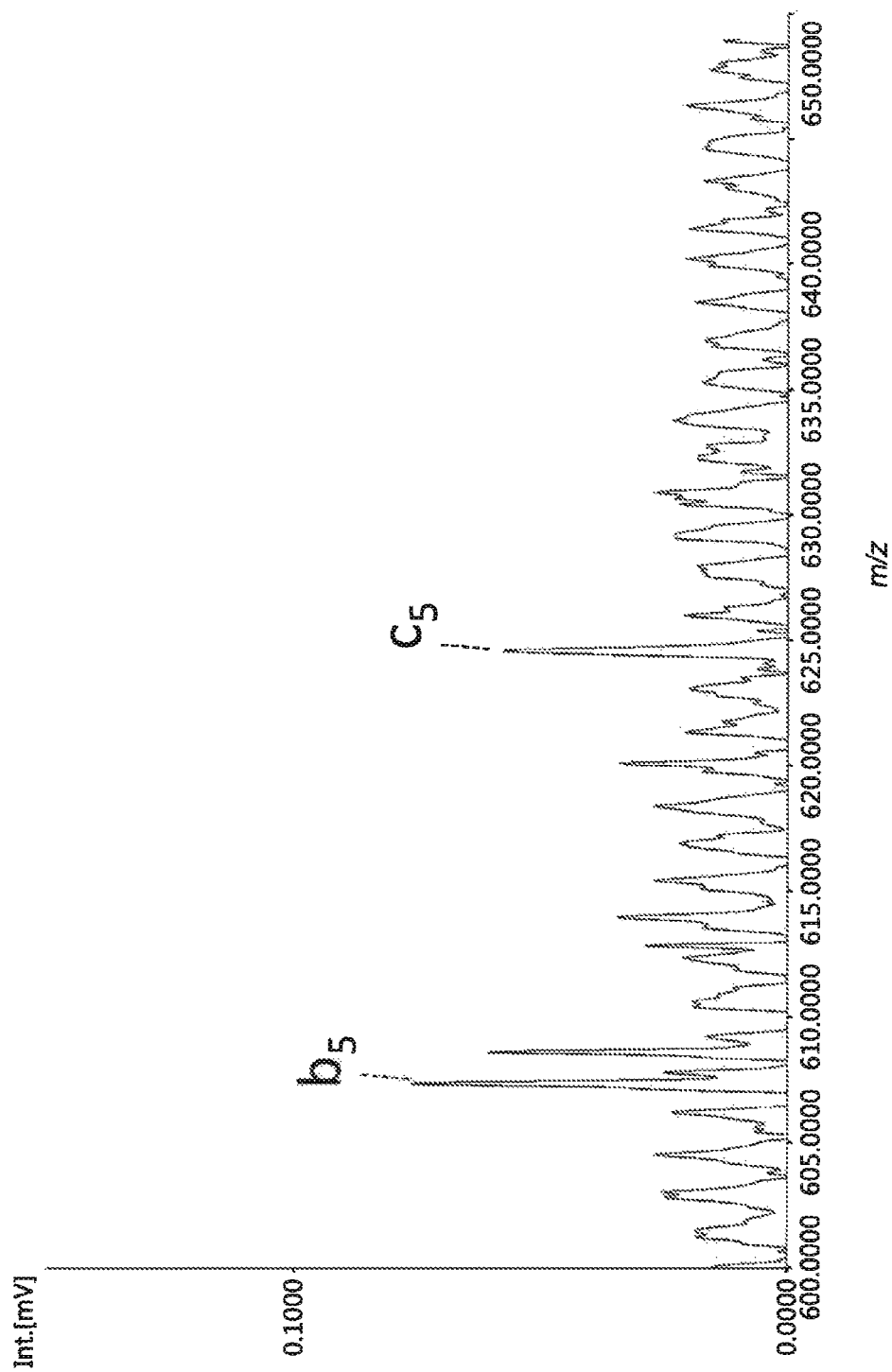
FIG. 4 is a measured example of the peak spectrum of the fragment ions.

According to the measured result shown in FIG. 3, even when the flow rate of the hydrogen radicals was at the lowest level of $4 \times 10^{10}$ [atoms/s], the peak intensity of the fragment ion reached approximately 0.1% of the peak intensity of the precursor ion. In other words, a fragment peak with an SN ratio of approximately 3.5 was obtained, which is a satisfactorily detectable level of peak intensity. FIG. 4 is a measured example of the mass spectrum in which a peak of this fragment ion appeared. This mass spectrum also demonstrates that the $c_5$ fragment ion peak is satisfactorily detectable.

In this actual measurement, the hydrogen radicals were cast into the ion trap 2 for 60 seconds. This value was chosen because the highest intensity of the $c_5$ fragment ion peak was obtained with this value under the condition that the hydrogen radicals were supplied at the highest flow rate ($1.3 \times 10^{12}$ [atoms/s]) in this measurement. Under these conditions, casting the hydrogen radicals for a period of time longer than 60 seconds conversely resulted in a decrease in the peak intensity of the fragment ion. A likely reason for this decrease is because the rate of increase in the amount of fragment ions newly generated by the dissociation is exceeded by the rate of decrease in the amount of fragment ions generated by the primary dissociation, due to the progress of the additional, multiple-stage dissociation of the fragment ions which have already undergone dissociation. It is easy to infer that this phenomenon can be utilized the other way around; i.e., if the period of time for casting the hydrogen radicals is sufficiently elongated, the dissociation will eventually reach the level of the individual amino acid residues (immonium ions).

As noted earlier, in the case of the ETD or ECD, the valence of the fragment ion decreases every time the ion is dissociated. Therefore, the technique of repeatedly dissociating an ion by the ETD or ECD to eventually obtain immonium ions can only be applied to an ion whose valence is greater than the number of amino acid residues. By comparison, in the case of the present invention, since the hydrogen radicals used in the dissociation process are electrically neutral, repeating the dissociation does not decrease the valence of the fragment ion. Therefore, when necessary, immonium ions can be generated by sufficiently elongating the period of time for casting the hydrogen radicals. Accordingly, the dissociation method used in the present invention is useful for a structural analysis which uses immonium ions.

The length of the casting time necessary for generating immonium ions can be previously determined through experiments.

Conversely, if the multiple-stage dissociation of the already dissociated ions needs be suppressed, it is preferable to apply, to the end-cap electrodes 22 and 24, a low-amplitude resonant excitation voltage (FNF signal) having a wide band of frequency components corresponding to a mass-to-charge-ratio range exclusive of the mass-to-charge ratio of the precursor ions while the hydrogen radicals are being cast onto the ions. This operation causes an excitation of the fragment ions generated by the dissociation of the precursor ions, with at least a portion of the fragment ions being displaced from the region into which the hydrogen radicals are cast within the ion trap 2. To further clarify, the density of the fragment ions within the region into which the hydrogen radicals are cast is decreased, so that the reaction between the fragment ions and the hydrogen radicals is suppressed. Consequently, the collection efficiency of the fragment ions generated by the primary dissociation is improved.

In the mass spectrometer of the present embodiment, a radical particle discharge hole 27 is provided on the same straight line as the radical particle introduction hole 26 for introducing hydrogen radicals into the ion trap 2. Therefore, most of the hydrogen radicals which have been cast into the ion trap 2 are directly discharged to the outside of the ion trap 2 after passing through the central region of the ion trap 2. Providing the radical particle discharge hole 27 in this manner produces the effect that the gas introduced into the ion trap 2 along with the hydrogen radicals is quickly discharged through this hole 27 to the outside of the ion trap 2, whereby an increase in the residual gas pressure within the ion trap 2 is prevented. This lowers the risk of an electric discharge which occurs if a high amount of voltage is applied to the electrodes 21, 22 and 24 under a deteriorated degree of vacuum. It also prevents a decrease in the ion-capturing efficiency as well as a decrease in the mass-resolving power in the mass-to-charge-ratio measurement process due to an increase in the gas pressure within the ion trap 2.

Figure 5:
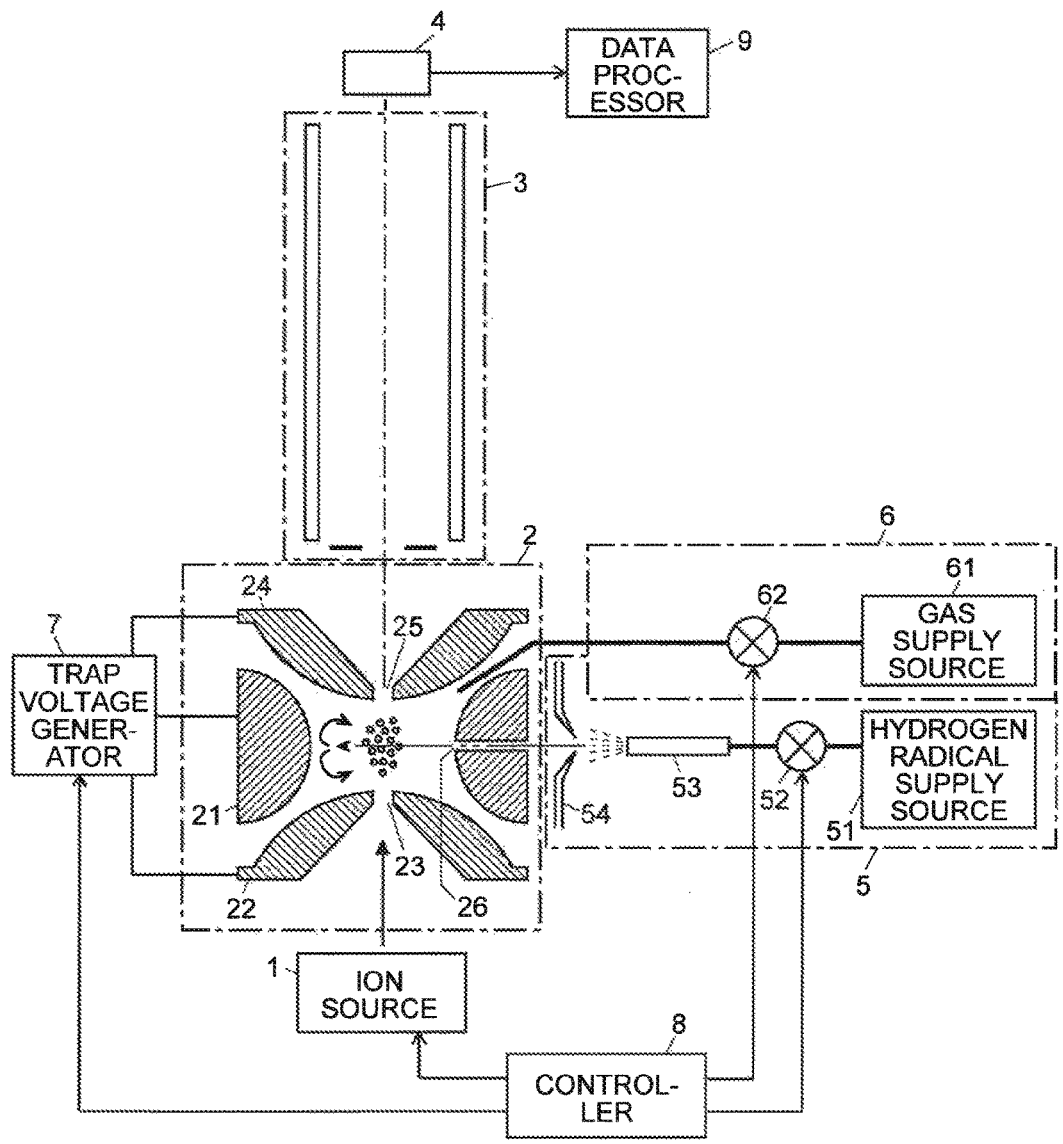
FIG. 5 is a schematic configuration diagram of a mass spectrometer as another embodiment of the ion analyzer according to the present invention.

However, this configuration may also be modified so as to help the hydrogen radicals reside in the ion trap 2, as in the normal gas-introduction process. Specifically, a ring electrode 21 with no radical particle discharge hole 27 may be used, as shown in FIG. 5. According to this configuration, the hydrogen radicals introduced into the ion trap 2 repeatedly collide with the inner wall of the ion trap 2, to be eventually discharged to the outside of the ion trap 2. Since the hydrogen radicals confined in the ion trap 2 can contribute to the reaction many times until they are discharged, the flow rate of the hydrogen radicals necessary for the ion dissociation can be lower than in the configuration in which the hydrogen radicals are quickly discharged from the ion trap 2, as in the embodiment shown in FIG. 1. In other words, the configuration shown in FIG. 5 requires a lower level of hydrogen-radical flow rate to produce an effect comparable to the one obtained at the minimum level of hydrogen-radical flow rate derived from the result shown in FIG. 3 ($4 \times 10^{10}$ [atoms/s]).

This point is hereinafter described in more detail. In the mass spectrometer of the present embodiment shown in FIG. 1, the effective density $N_A$ [atoms/m³] of the hydrogen radicals which react with the ions in the ion trap 2 is expressed by the following equation (1):

$$N_A = I_A/(v\pi R^2) \tag{1}$$

where $I_A$ is the flow rate [atoms/s] of the hydrogen radicals, v is the velocity [m/s] of the hydrogen radicals, and R is the radius [m] of the hydrogen-radical flux. In the experiment shown in FIG. 3, the hydrogen radicals were generated by heating hydrogen gas. Since the heating temperature was 2000 K, v is estimated at approximately 7000 m/s. Using the radius of the radical particle introduction hole 26 of the ion trap 2 (0.75 mm) as the value of R and assigning the minimum value of the flow rate of the hydrogen radicals ($4 \times 10^{10}$ [atoms/s]) to $I_A$ in equation (1) demonstrates that the minimum value of $N_A$ in the experiment shown in FIG. 3 is $3 \times 10^{12}$ [atoms/m³]. That is to say, the density of the hydrogen radicals which corresponds to the minimum value of the hydrogen-radical flow rate derived from the result of FIG. 3 is $3 \times 10^{12}$ [atoms/m³].

On the other hand, in the mass spectrometer according to the other embodiment shown in FIG. 5, the stationary solution of the density $N_B$ [atoms/m³] of the hydrogen radicals involved in the reaction can be determined by solving the rate equation, as expressed by equation (2):

$$dN_B/dt = (I_B/V) - (N_B/\tau) = 0 \rightarrow N_B = \tau(I_B/V) \tag{2}$$

where $I_B$ is the flow rate [atoms/s] of the hydrogen radicals, V is the inner volume [m³] of the ion trap 2, and $\tau$ is the confinement time [sec] for which the discharging and recombination of hydrogen radicals are both taken into account. Provided that the influence of the particle temperature of the hydrogen radicals on the reaction can be ignored, the same dissociation effect can be obtained with both of the configurations of FIGS. 1 and 5 if the densities $N_A$ and $N_B$ are equal to each other. From this relationship, the ratio $\alpha$ between the flow rates of the hydrogen radicals necessary for the respective configurations can be obtained, as expressed by the following equation (3):

$$I_A/(v\pi R^2) = \tau(I_B/V) \rightarrow \alpha \equiv I_B/I_A = (1/\tau)V/(v\pi R^2) \tag{3}$$

Suppose that the inner region of the ion trap 2 can be approximated by a sphere. On the assumption that the radius of this sphere is 10 mm, R=0.75 mm and v=7000 m/s (equivalent to 2000 K), $\alpha$ in equation (3) is expressed by the following equation (4):

$$\alpha \approx 3 \times 10^{-4}/\tau \tag{4}$$

Equation (4) demonstrates that, if the confinement time $\tau$ is longer than 300 μsec, the configuration of FIG. 5 requires a lower flow rate of hydrogen radicals (or lower density of hydrogen radicals) to produce a dissociation effect comparable to the configuration of FIG. 1. A preferable method for elongating the confinement time $\tau$ is to coat the inner wall surfaces of the electrodes 21, 22 and 24 of the ion trap 2 with a material on which the recombination of the hydrogen radicals barely occurs, such as silicon dioxide ($SiO_2$). As is generally known, hydrogen radicals easily recombine into hydrogen molecules upon collision with the surface of the electrode 21, 22 or 24 of the ion trap 2. By coating the inner wall surfaces of the electrodes 21, 22 and 24 with an appropriate silicon dioxide layer, the probability of the recombination of the hydrogen radicals can be lowered. Additionally, the area ratio of the gas-discharging openings (the gaps between the electrodes 21, 22 and 24, as well as the openings of the ion introduction hole 23 and the ion ejection hole 25) to the inner surface area of the ion trap 2 should also preferably be reduced to decrease the discharging efficiency of the hydrogen radicals.

Needless to say, forming an appropriate coating layer on the inner wall surfaces of the electrodes 21, 22 and 24 of the ion trap 2 is also effective in the configuration of the embodiment shown in FIG. 1.

In the previous embodiments, the radical particle introduction hole 26 is formed in the ring electrode 21, and the hydrogen radicals are introduced through this hole into the ion trap 2. Alternatively, similarly to the cooling gas or other kinds of gas, the hydrogen radicals may also be introduced through a gas tube into the ion trap. However, hydrogen radicals easily recombine into hydrogen molecules upon coming in contact with the inner wall surface of the gas tube or other parts. Therefore, it is preferable to take measures to avoid such recombination.

For example, the gas tube may be entirely made of a material on which the recombination of the hydrogen radicals barely occurs, such as the aforementioned silicon dioxide, or the inner wall surface of the gas tube may be coated with a layer of silicon dioxide or other appropriate materials. Needless to say, the inner wall surface of the radical particle introduction hole 26 in the configuration of FIG. 1 or 5 should also be coated with a layer of silicon dioxide or other appropriate materials. By these measures, the loss of the hydrogen radicals in the process of transporting the hydrogen radicals to the inside of the ion trap 2 can be reduced.

It is also possible to form a stream of inert gas (e.g. helium) along the inner wall surface of the gas tube and pass the hydrogen radicals through the central region of this inert-gas stream so that the hydrogen radicals inside the gas tube will not come in contact with the inner wall surface of the tube.

In general, the rate of reaction between the ions and hydrogen radicals in the ion trap 2 depends on the temperature of the hydrogen radicals. Therefore, in the case of supplying hydrogen radicals through a gas tube into the ion trap 2 in the previously described manner, it is preferable to provide a heater or similar device to maintain the gas tube at high temperatures.

The previous embodiments are mere examples of the present invention, and any change, addition or modification appropriately made within the spirit of the present invention will naturally fall within the scope of claims of the present application.

For example, as opposed to the previous embodiments in which a three-dimensional quadrupole ion trap is used as the ion trap in the mass spectrometer, a multipole linear ion trap may be used. For an efficient dissociation of the ions within an ion trap, the density of the ions captured in the ion trap should be as high as possible. In general, as compared to three-dimensional quadrupole ion traps, linear ion traps are less affected by space charge and therefore can achieve a higher surface density of the ions. Additionally, injecting the hydrogen radicals along the longitudinal axis of a linear ion trap provides a longer flight distance for the hydrogen radicals to contribute to the reaction. For these reasons, using a linear ion trap is advantageous in terms of the dissociation efficiency.

An ion trap is a device which confines ions by the effect of a radio-frequency electric field. It is also possible to cast hydrogen radicals onto the ions confined in the cell of a Fourier transform ion cyclotron resonance mass spectrometer or similar device which confines ions by the effect of a magnetic field. Needless to say, confining the ions in a specified space is not always necessary; for example, it is possible to induce the dissociation in a stream of ions by casting hydrogen radicals in an oblique direction across the stream, in the same direction as the stream, or in the opposite direction to the stream.

Furthermore, although the previous embodiments are a mass spectrometer which performs mass spectrometry on fragment ions generated by dissociation, it is evident that the present invention is also applicable in an ion mobility spectrometer which detects fragment ions after separating them according to their degrees of ion mobility, or an ion mobility mass spectrometer which initially separates fragment ions according to their degrees of ion mobility, and then additionally separates them according to their mass-to-charge ratios, to separately detect each fragment ion.

REFERENCE SIGNS LIST

1 . . . Ion Source
2 . . . Ion Trap
21 . . . Ring Electrode
22, 24 . . . End-Cap Electrode
23 . . . Ion Introduction Hole
25 . . . Ion Ejection Hole
26 . . . Radical Particle Introduction Hole
27 . . . Radical Particle Discharge Hole
3 . . . Mass Separator
4 . . . Ion Detector
5 . . . Hydrogen Radical Irradiator
51 . . . Hydrogen Radical Supply Source
52, 62 . . . Valve
53 . . . Nozzle
54 . . . Skimmer
6 . . . Gas Supplier
61 . . . Gas Supply Source
7 . . . Trap Voltage Generator
8 . . . Controller

The invention claimed is:

1. An ion analyzer for analyzing fragment ions generated by dissociating an ion derived from a sample component, comprising:
an ion confinement section having a space in which an ion is confined by a radio-frequency electric field or a magnetic field;
an ion source for introducing an ion derived from a target sample component into the space;
a hydrogen radical irradiator configured to introduce hydrogen radicals at a flow rate of $4 \times 10^{10}$ [atoms/s] or higher into the space where the ion is present in order to dissociate the ion;
a separator configured to separate ions ejected from the space into fragment ions according to at least either mass-to-charge ratios or mobility of the fragment ions; and
an ion detector configured to detect the fragment ions.

2. The ion analyzer according to claim 1, wherein:
a neutral particle is introduced into the space within at least either a period of time before an introduction of the hydrogen radicals or a period of time after the introduction.

3. The ion analyzer according to claim 1, further comprising a laser light irradiator configured to cast laser light onto the ion captured within the space, within at least either a period of time before an introduction of the hydrogen radicals or a period of time after the introduction.

4. The ion analyzer according to claim 1,
further comprising a gas supplier configured to introduce a cooling gas into the space before introducing the hydrogen radicals into the space.

5. The ion analyzer according to claim 1,
further comprising a voltage generator configured to apply a resonant excitation voltage to the space to lower a rate of reaction of the ion and the hydrogen radicals by resonantly exciting ions included in a mass-to-charge-ratio range exclusive of a precursor ion, at least during a portion of a period of time for introducing the hydrogen radicals into the space.

6. The ion analyzer according to claim 1, wherein:
the hydrogen radical irradiator sets a long period of time for the introduction of the hydrogen radicals so as to make the ion undergo dissociation a plurality of times.

7. The ion analyzer according to claim 1, wherein:
the hydrogen radical irradiator includes a hydrogen-radical introduction tube for transporting the hydrogen radicals to a region where the ion is present, the hydrogen-radical introduction tube being either a glass tube or a tube having a glass coating formed at least on an inner wall surface of the tube.

8. The ion analyzer according to claim 1, wherein:
the hydrogen radical irradiator includes a hydrogen-radical introduction tube for transporting the hydrogen radicals to a region where the ion is present and a heater for maintaining the hydrogen-radical introduction tube at high temperatures or heating the same tube.

9. The ion analyzer according to claim 1, wherein:
the hydrogen radical irradiator forms a stream of inert gas along an inner wall surface of a hydrogen-radical introduction tube for transporting the hydrogen radicals to a region where the ion is present, in such a manner that the stream of inert gas prevents the hydrogen radicals from coming in contact with the inner wall surface of the introduction tube while the hydrogen radicals are transported to the region where the ion is present.

10. The ion analyzer according to claim 1, wherein:
the hydrogen radical irradiator includes a flux shaper for extracting a directional stream of the hydrogen radicals.

11. An ion analyzer for analyzing fragment ions generated by dissociating an ion derived from a sample component, comprising:
an ion confinement section having a space in which an ion is confined by a radio-frequency electric field or a magnetic field;
an ion source for introducing an ion derived from a target sample component into the space;
a hydrogen radical irradiator configured to introduce hydrogen radicals at a density of $3\times10^{12}$ [atoms/m$^3$] or higher into the space where the ion is present in order to dissociate the ion;
a separator configured to separate ions ejected from the space into fragment ions according to at least either mass-to-charge ratios or mobility of the fragment ions; and
an ion detector configured to detect the fragment ions.

12. The ion analyzer according to claim 11, wherein:
a neutral particle introduced is into the space within at least either a period of time before an introduction of the hydrogen radicals or a period of time after the introduction.

13. The ion analyzer according to claim 11,
further comprising a laser light irradiator configured to cast laser light onto the ion captured within the space, within at least either a period of time before an introduction of the hydrogen radicals or a period of time after the introduction.

14. The ion analyzer according to claim 11,
further comprising a gas supplier configured to introduce a cooling gas into the space before introducing the hydrogen radicals into the space.

15. The ion analyzer according to claim 11, wherein:
further comprising a voltage generator configured to apply a resonant excitation voltage to the space to lower a rate of reaction of the ion and the hydrogen radicals by resonantly exciting ions included in a mass-to-charge-ratio range exclusive of a precursor ion, at least during a portion of a period of time for introducing the hydrogen radicals into the space.

16. The ion analyzer according to claim 11, wherein:
the hydrogen radical irradiator sets a long period of time for the introduction of the hydrogen radicals so as to make the ion undergo dissociation a plurality of times.

17. The ion analyzer according to claim 11, wherein:
the hydrogen radical irradiator includes a hydrogen-radical introduction tube for transporting the hydrogen radicals to a region where the ion is present, the hydrogen-radical introduction tube being either a glass tube or a tube having a glass coating formed at least on an inner wall surface of the tube.

18. The ion analyzer according to claim 11, wherein:
the hydrogen radical irradiator includes a hydrogen-radical introduction tube for transporting the hydrogen radicals to a region where the ion is present and a heater for maintaining the hydrogen-radical introduction tube at high temperatures or heating the same tube.

19. The ion analyzer according to claim 11, wherein:
the hydrogen radical irradiator forms a stream of inert gas along an inner wall surface of a hydrogen-radical introduction tube for transporting the hydrogen radicals to a region where the ion is present, in such a manner that the stream of inert gas prevents the hydrogen radicals from coming in contact with the inner wall surface of the introduction tube while the hydrogen radicals are transported to the region where the ion is present.

20. The ion analyzer according to claim 11, wherein:
the hydrogen radical irradiator includes a flux shaper for extracting a directional stream of the hydrogen radicals.

* * * * *